(12) United States Patent
Groman

(10) Patent No.: US 6,398,628 B1
(45) Date of Patent: Jun. 4, 2002

(54) MICRO ABRASIVE BLASTING DEVICE AND METHOD WITH INTEGRAL FLOW CONTROL

(76) Inventor: Barry Boaz Groman, 1917 NW. 80 Ave., Margate, FL (US) 33063

( * ) Notice: Subject to any disclaimer, the term of this patent is extended or adjusted under 35 U.S.C. 154(b) by 0 days.

(21) Appl. No.: 09/897,286

(22) Filed: Jul. 2, 2001

Related U.S. Application Data

(63) Continuation of application No. 09/702,270, filed on Oct. 30, 2000.

(51) Int. Cl.$^7$ .............................. B24C 3/00; B24C 5/04
(52) U.S. Cl. ........................................ 451/90; 451/102
(58) Field of Search .............................. 451/38, 39, 101, 451/102, 90, 99, 75; 72/53; 241/40

(56) References Cited

U.S. PATENT DOCUMENTS

| | | |
|---|---|---|
| 2,441,441 A | 5/1948 | Paasche |
| 2,577,465 A | 12/1951 | Jones et al. |
| 4,475,370 A | 10/1984 | Stark et al. |
| 4,941,298 A | 7/1990 | Fernwood et al. |
| 5,839,946 A | 11/1998 | Hertz |
| 6,004,191 A | 12/1999 | Schur et al. |

FOREIGN PATENT DOCUMENTS

WO PCT/US96/11696 2/1997

Primary Examiner—Derris H. Banks

(57) ABSTRACT

The present invention is a superior micro abrasive blasting device (55) with an integral flow control mechanism. Flow control is achieved through the displacement of discharge conduit (10) to control the distance between discharge conduit inlet (12) and mixing chamber second end wall (30). The flow control mechanism provides for the continuous pressurization of the mixing chamber (23) to yield instantaneous flow start-up response and instantaneous flow shut-off response. A method is provided for maintaining discharge conduit outlet (67) stationary with respect to target material (40) while discharge conduit inlet (12) is displaced. The method utilizes the deflection properties of discharge conduit (10) to provide the necessary compliance so the discharge conduit inlet (12) can be displaced while the discharge conduit outlet (12) remains stationary. The deflection properties of the discharge conduit (10) are also utilized to provide a sealing force between discharge conduit inlet (12) and mixing chamber second end wall (30). The sealing force assures that discharge conduit inlet (12) abuts mixing chamber second end wall (30) when the device is not operational. The deflection properties of discharge conduit (10) are also utilized to apply a displacement restoring force on discharge conduit (10) to close the distance between discharge conduit inlet (12) and mixing chamber second end wall (30) when the device is operational.

21 Claims, 13 Drawing Sheets

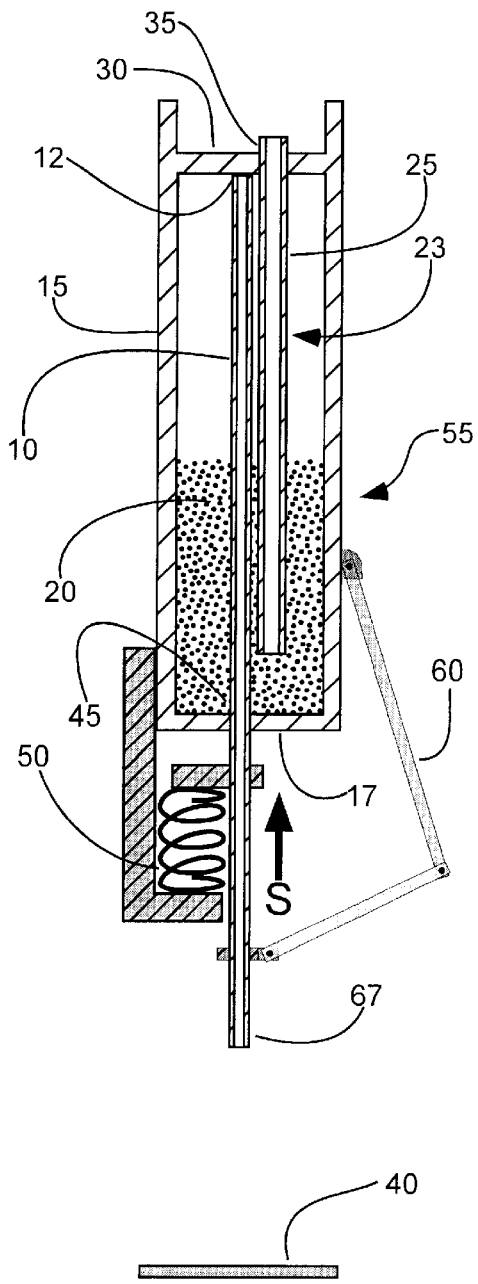
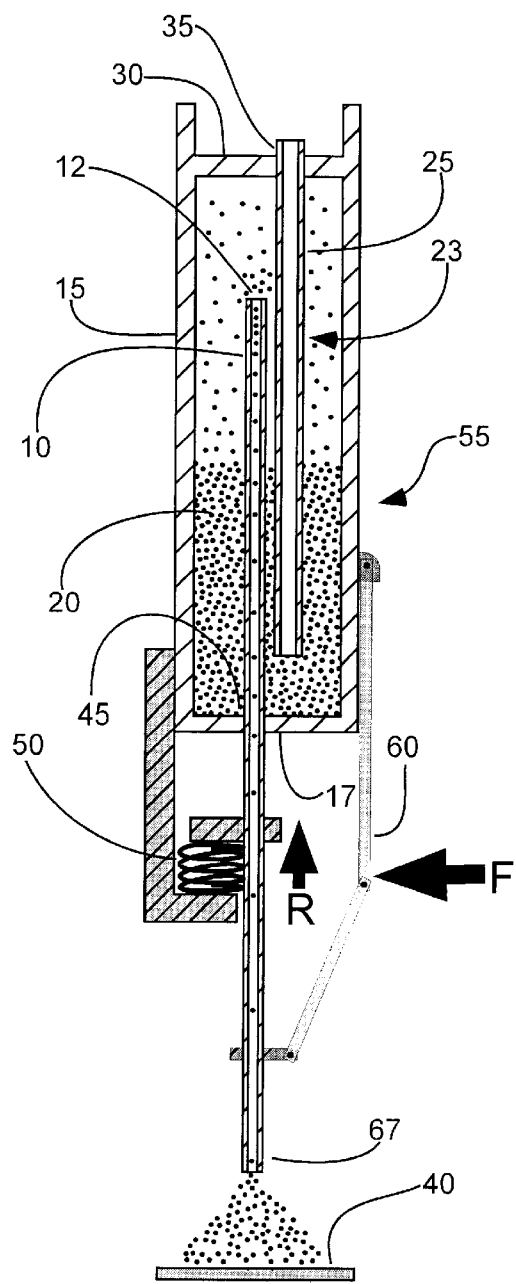
*FIG. 1A*  *FIG. 1B*

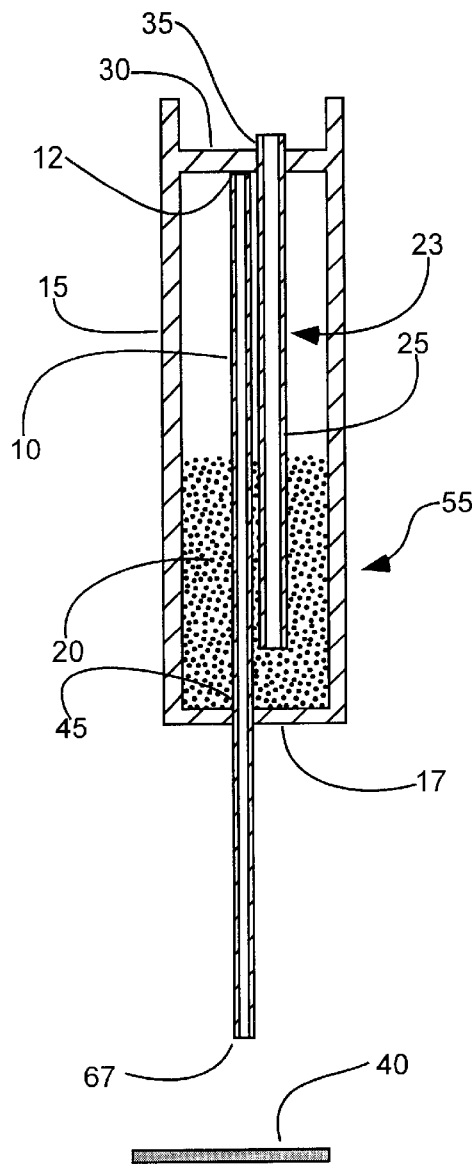
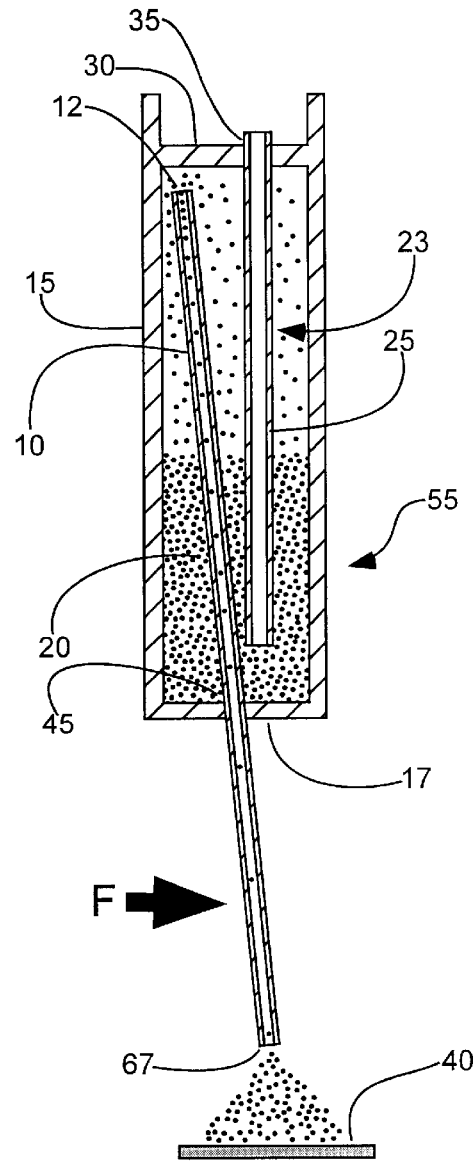
FIG. 2A                    FIG. 2B

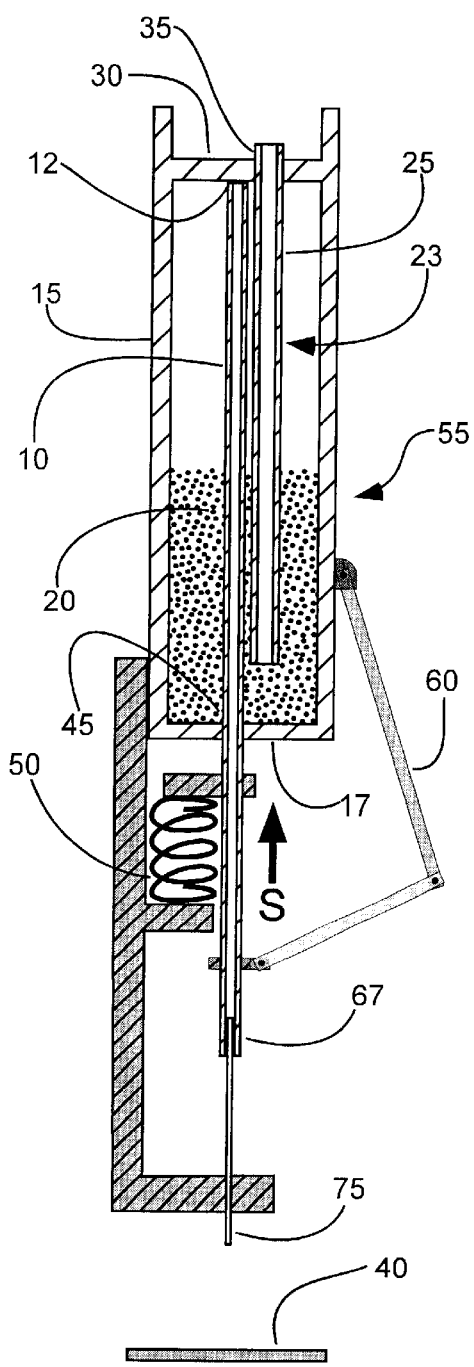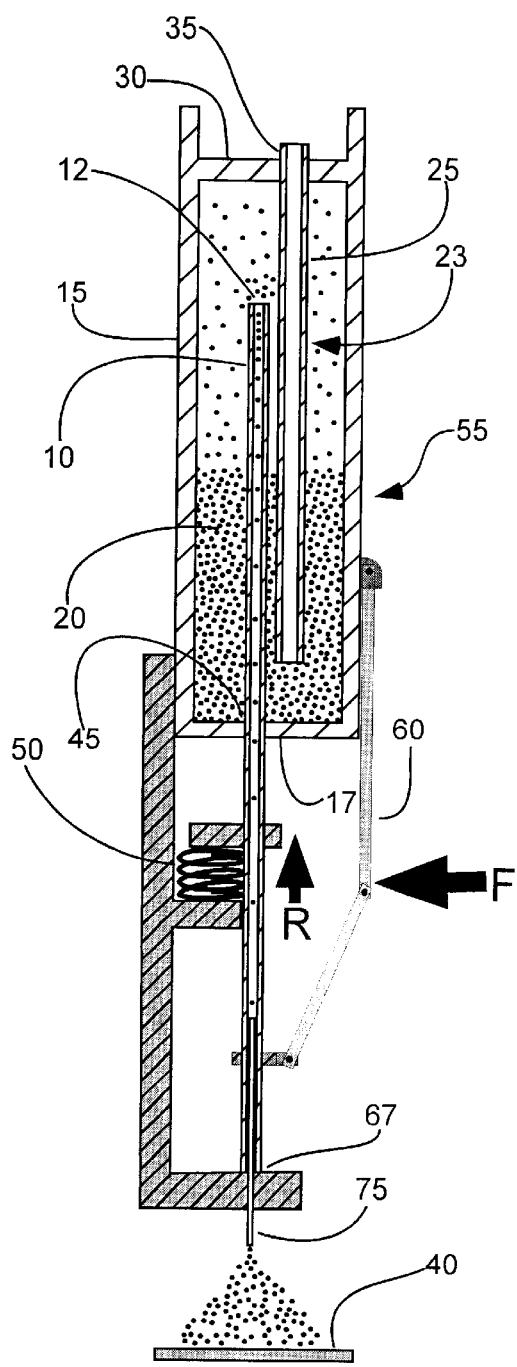
*FIG. 4A*  *FIG. 4B*

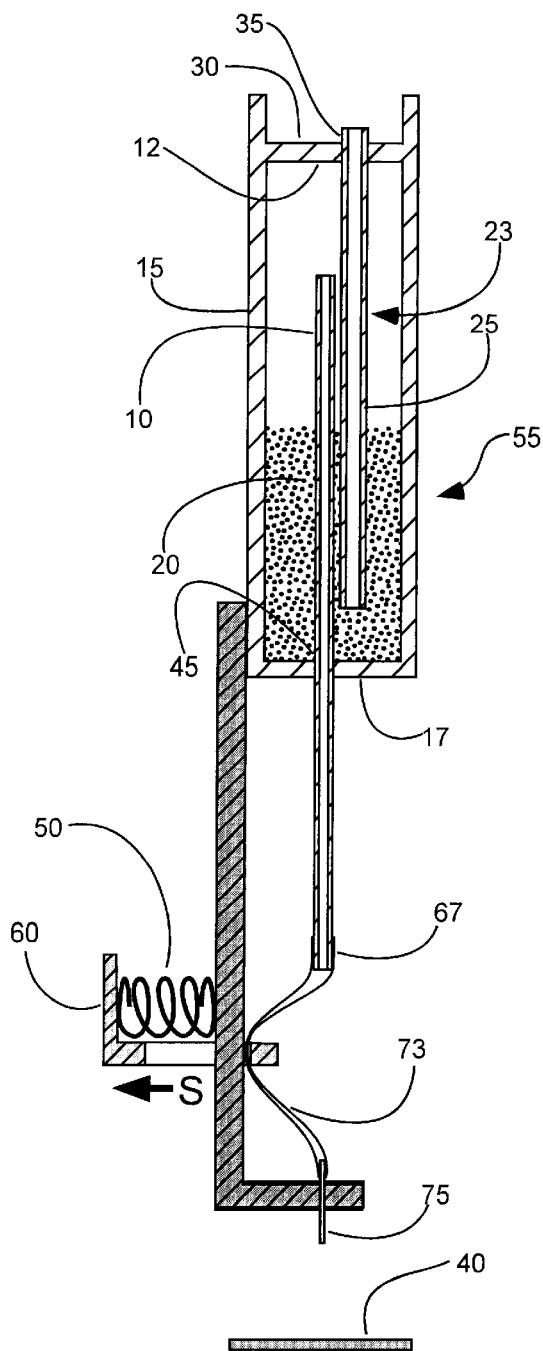
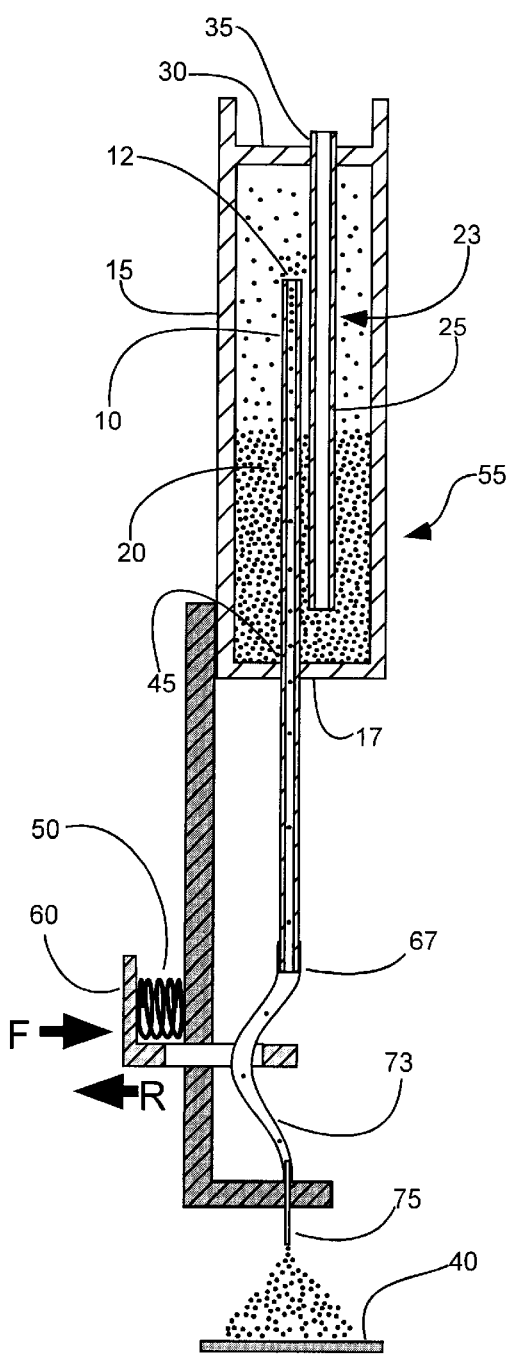
*FIG. 6A*  *FIG. 6B*

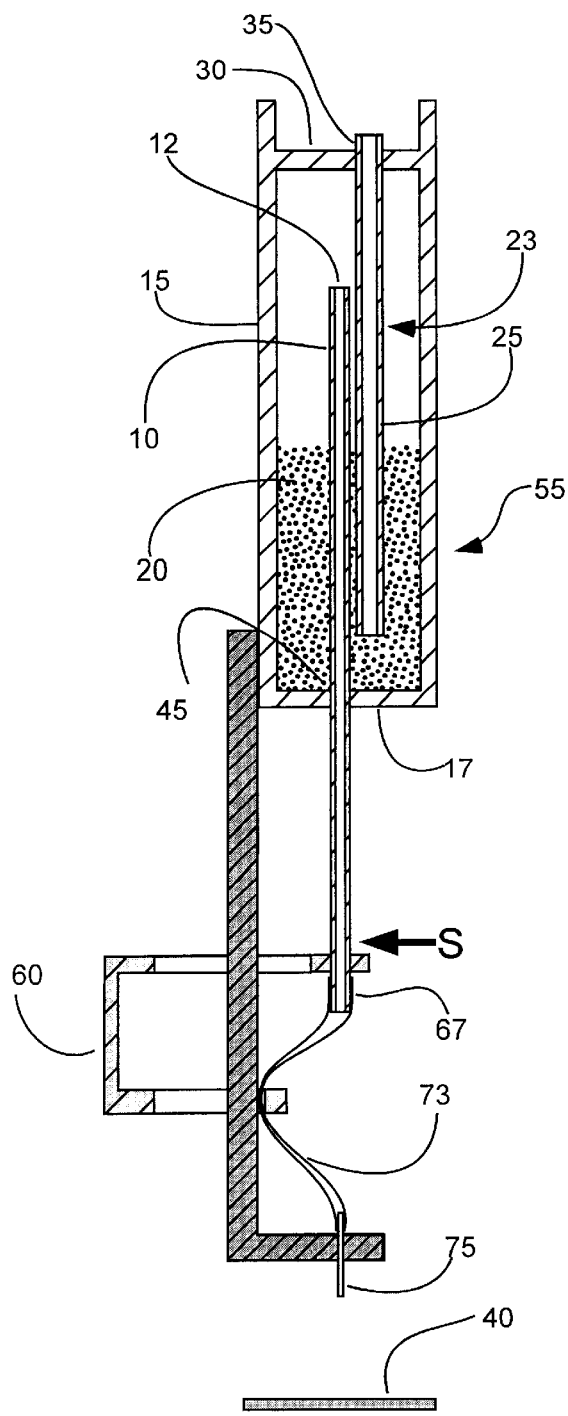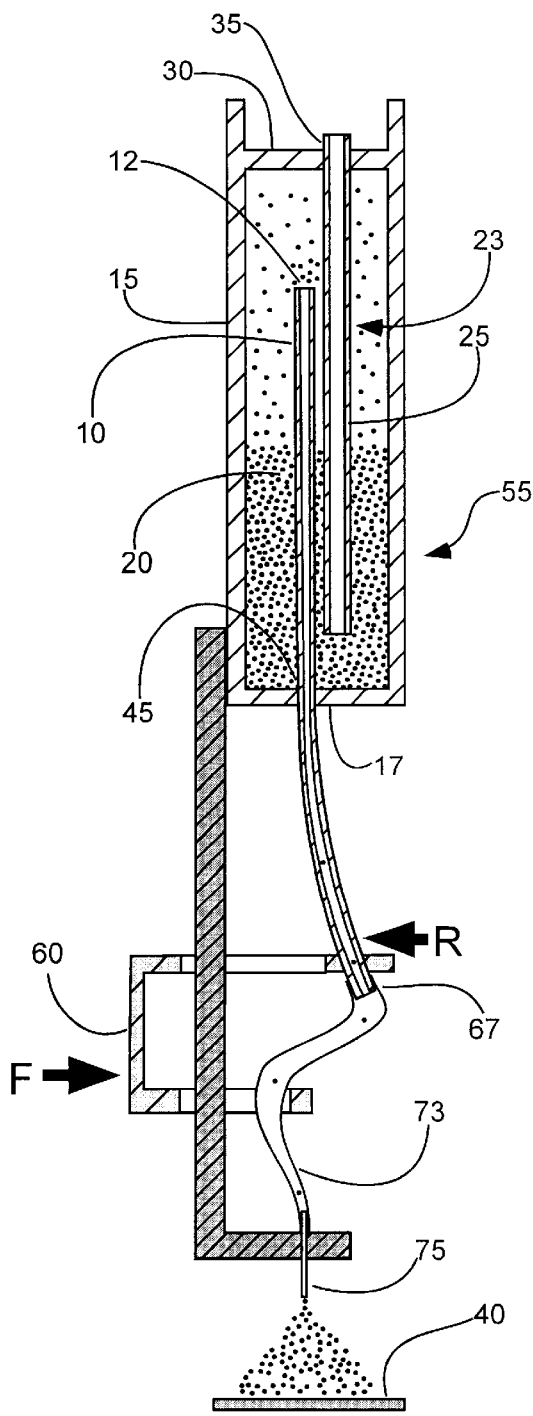
*FIG. 7A*  *FIG. 7B*

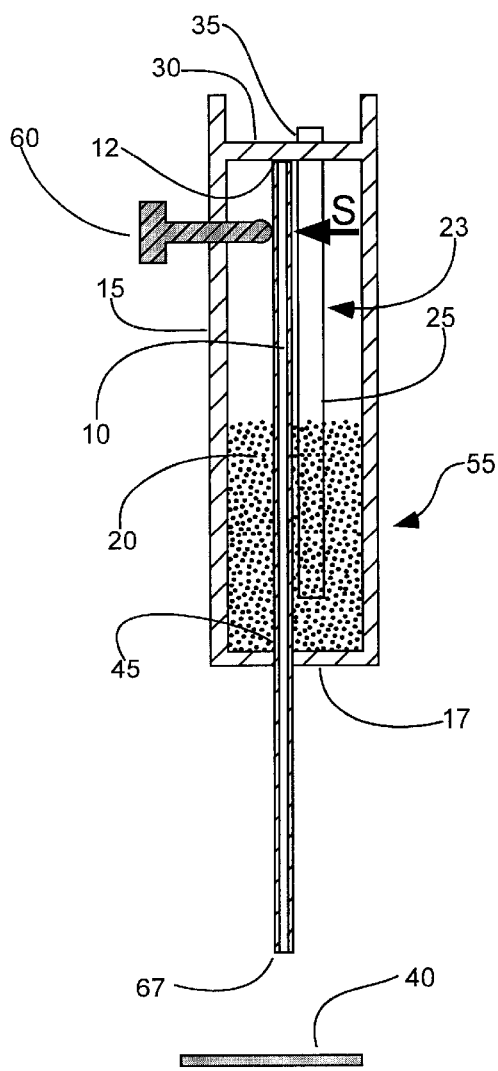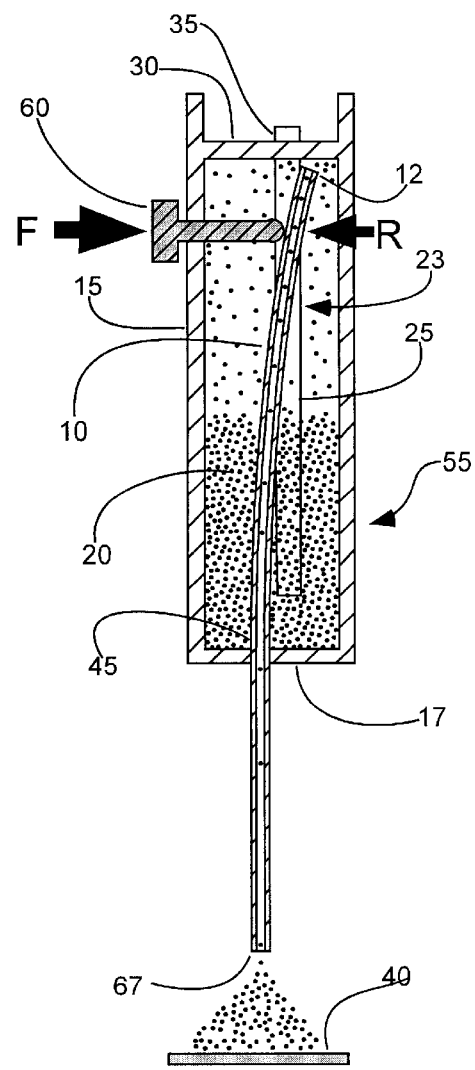
*FIG. 8A*  *FIG. 8B*

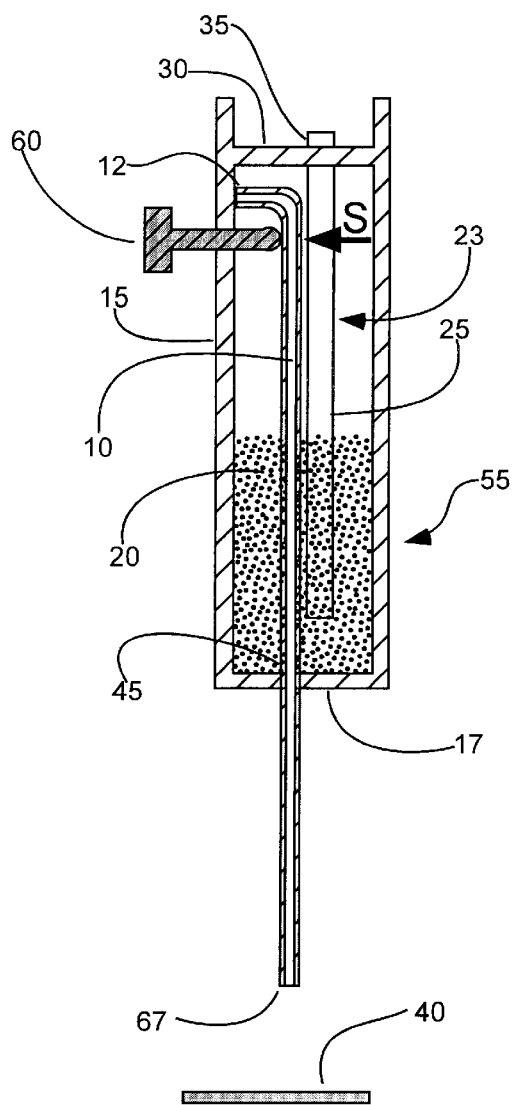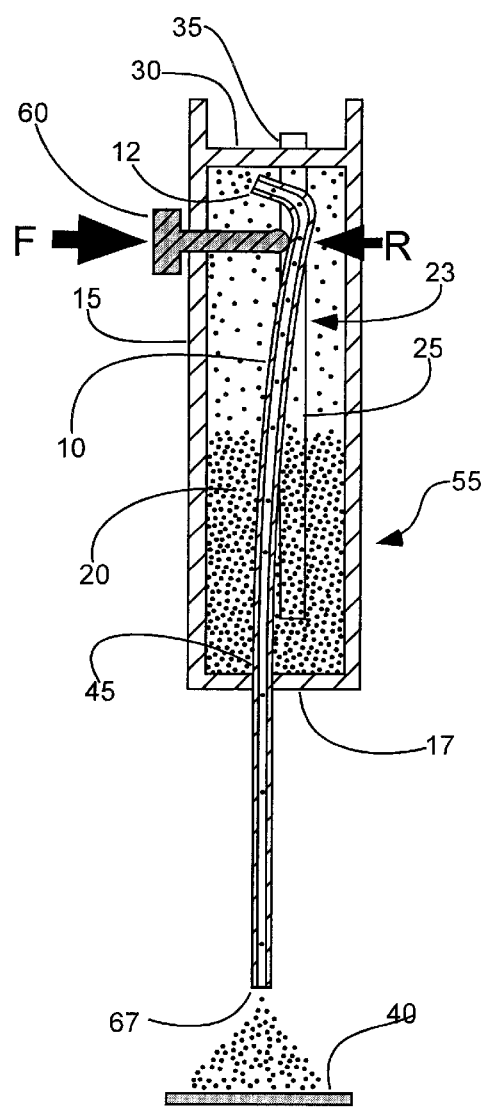
*FIG. 9A*
*FIG. 9B*

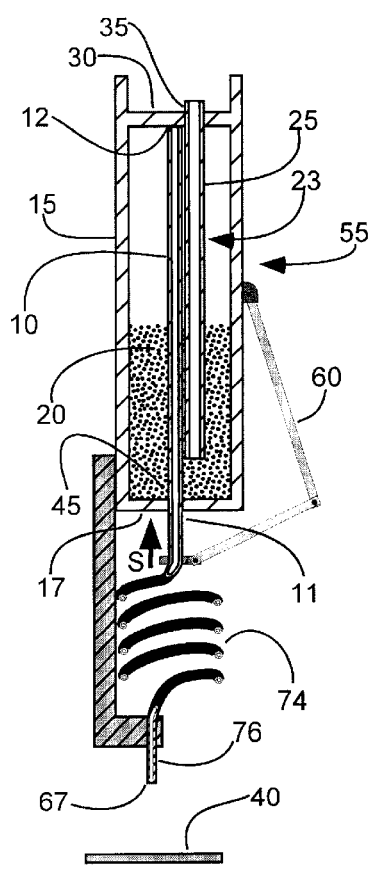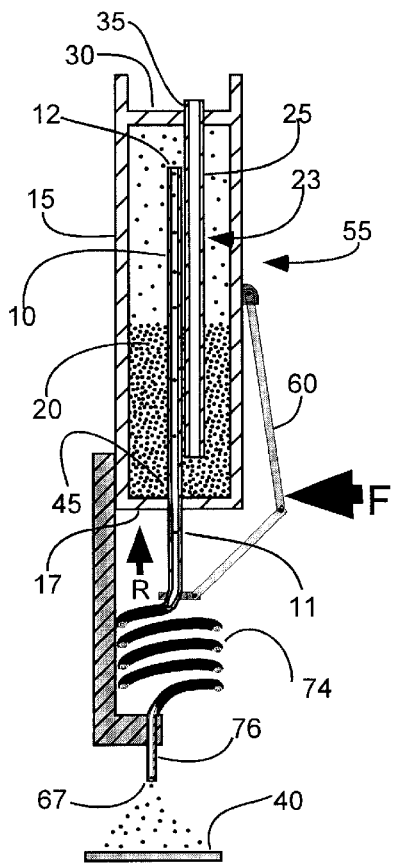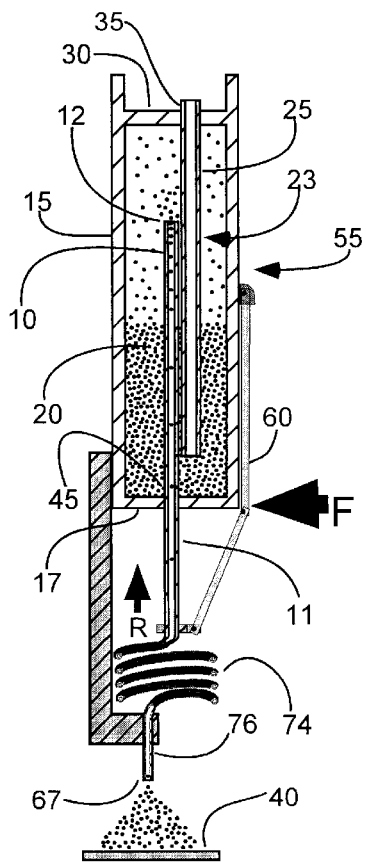
*FIG. 10A*  *FIG. 10B*  *FIG. 10C*

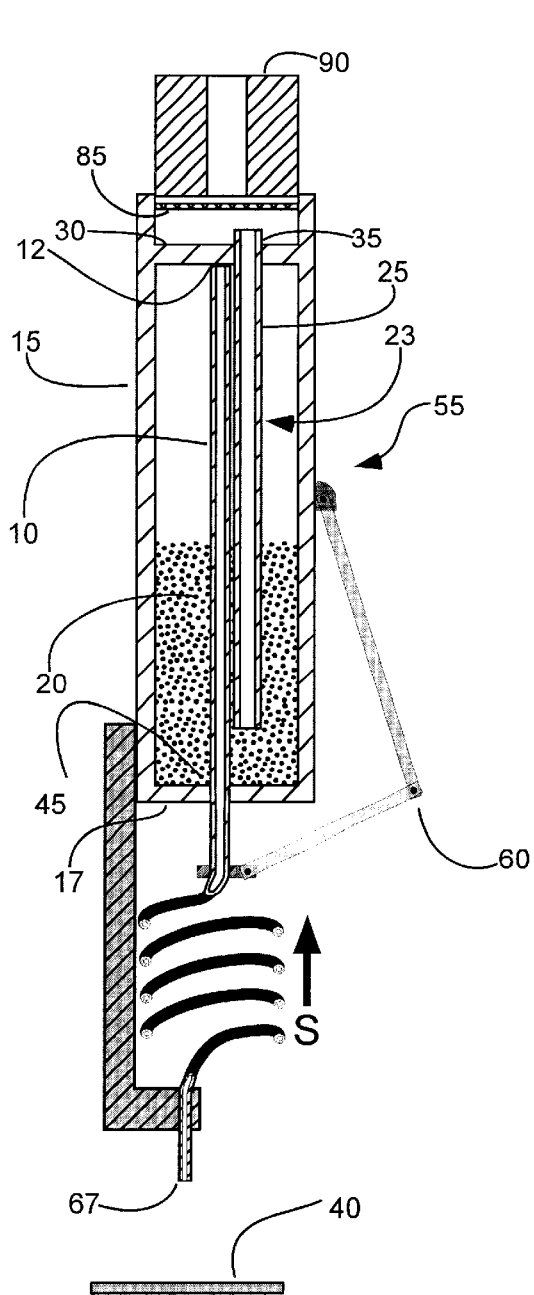
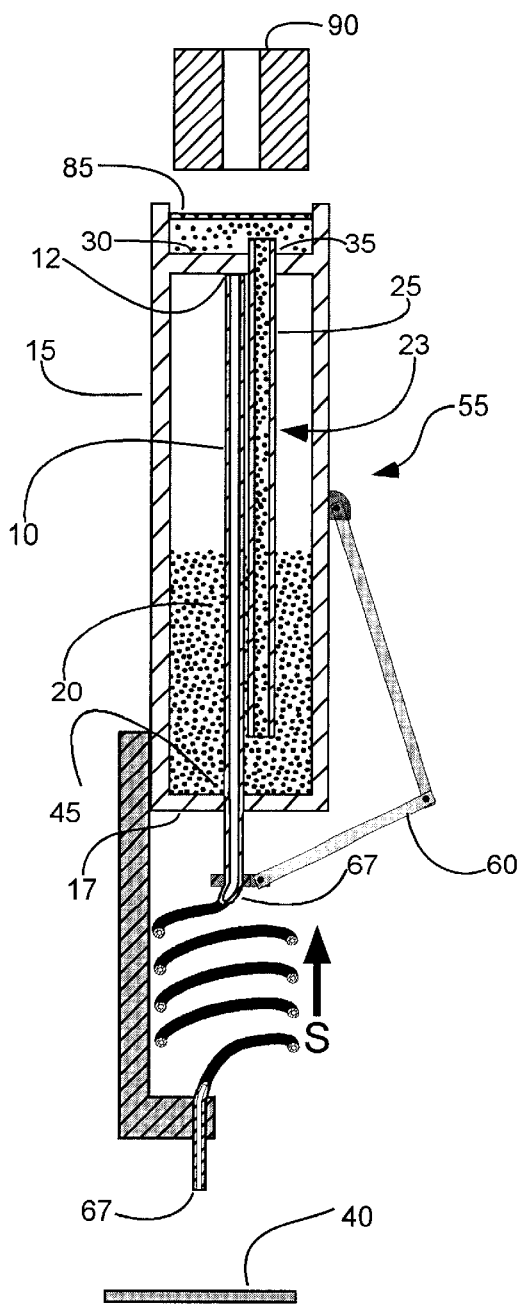
*FIG. 12A*  *FIG. 12B*

MICRO ABRASIVE BLASTING DEVICE AND METHOD WITH INTEGRAL FLOW CONTROL

This applications a continuation of U.S. application Ser. No. 09/702,270, filed Oct. 30, 2000.

BACKGROUND OF THE INVENTION

The present invention relates generally to the field of devices for propelling particulate matter with intent to etch the surface of a target material. More specifically, the present invention relates to a micro abrasive blasting device powered by a pressurized-gas source for use with dental procedures.

Abrasive blasting devices operate on the physical property that gas at a higher pressure flows towards and into gas at lower pressure. When particulate matter is mixed with gas at higher pressure, the gas carries the particulate matter as the gas accelerates and flows to the lower pressure. As the gas and particulate matter blast the target material at high speed, the impact of the particles removes layers of the target material.

This process of material removal is commonly known as etching and also as sandblasting. As the rate of the target material removal increases, the etching process can be utilized for drilling and cutting. More specifically, the aggressiveness of the particulate impact-speed and frequency determine the rate of material removal, and thus whether an abrasive blasting device is useful for polishing, etching, or drilling. Particulate impact-speed and frequency are adjusted by variation of the gas flow rate and gas-to-particulate mixture ratio.

In dentistry this technology is known as micro-abrasion and is used to achieve a variety of goals—such as to remove foreign material or to dull a shiny surface, roughen or etch the surface to enhance bonding quality, and to remove decay by drilling and cutting tooth structure. Such delicate procedures performed intra-oral require instantaneous response and precise control over the flow of the particle stream to assure that no damage due to over-etching or material scatter occur.

As disclosed in pending U.S. patent application Ser. No. 09/702,270, filled Oct. 30, 2000, great advantages are found over existing abrasion devices by preventing the particulate matter from entering the discharge conduit prior to device use. In addition, the pending application discloses that the regulation of the discharge conduit inlet opening provides a superior method for flow control. Specifically, that the position of the closure cap determines the distance to the discharge conduit inlet, where the gap between the closure cap and the discharge conduit inlet determines the gas-abrasive mixing and flow rate. Adjusting the gap between the closure cap and the discharge conduit inlet regulates these gas-abrasive flow characteristics.

In practice, however, the inventor has determined that the adjustment of the gap between the closure cap and the discharge conduit inlet via displacement of the closure cap was good for flow rate regulation but not for dynamic flow rate control during operation. It was found that the user must use both hands to adjust the closure cap position. That is a result of the cap residing at the pressurized-gas source delivery side of the device—opposite the discharge nozzle; hence to adjust the closure cap positioning requires the use of a second hand while the first aims the nozzle at the target material.

Improvements on the original patent application are disclosed herein, that facilitate dynamic flow-control during operation using only a single-hand. Existing etching devices use various forms of flow control that reside on the pressurized-gas supply lines upstream of the mixing chamber. The flow control method disclosed herein resides downstream of the mixing chamber. Additionally, the improvements disclosed herein eliminate the need for the discharge conduit cap disclosed in the original patent application, further simplifying the device.

One device that also requires two hands to operate is the Paasche device, U.S. Pat. No. 2,441,441. The Paasche device is still widely used by dentists and provides two flow control mechanisms. The device utilizes a screw mounted into the reservoir closure cap to regulate the amount of abrasive contained in the air stream (Page 3 Col. 1 Lines 46–51). The screw is manually adjusted to regulate the gas-abrasive mixture by providing means for varying the gap between the screw tip and gas-abrasive exit tube. For activating the pressurized-gas flow, a separate on-off valve is provided upstream of the mixing chamber (Page 3 Col. 1 Lines 14–23). To dynamically adjust the airflow of the Passche device, two hands are required. One hand is used to support the device and activate the on-off valve, while the second hand is used to adjust the position of the regulating screw.

The Fernwood et al. device, U.S. Pat. No. 4,941,298 provides a pinch lever mechanism for controlling the compressed air flow (Page 1 col. 2 lines 58–64). The pinch lever causes the compressed air inlet supply tube to collapse shut, thus inhibiting the airflow. This Fernwood et al. pinch lever control mechanism is functionally equivalent to the main control valve of the Jones et al. device U.S. Pat. No. 2,577,465. In Jones et al, the valve is also utilized to control the airflow upstream of the mixing chamber (Page 1, Col. 2, Line 7).

Some abrasion devices have no flow regulation mechanisms and are dependent solely on external flow-control mechanisms. These external flow-control mechanisms are very common in dentistry. Several of these controls exist at every dental chair and dental labs, since most dental instruments connect to a standard dental connector. These common dental flow-control means include on-off valves, flow-rate valves and pressure regulators. Many dental devices are controlled via a foot-operated flow-control valve, which sets the pressurized-gas flow rate delivered at the standard dental-chair connector.

The following apparatuses—by Stark et al., U.S. Pat. No. 4,475,370, Hertz, U.S. Pat. No. 5,839,946, Hertz PCT application 96/11696 filed on Jul. 15, 1996, and Schur et al. U.S. Pat. No. 6,004,191,—rely solely on external flow-control mechanisms upstream of the mixing chamber. These apparatuses provide for simple devices with no moving parts and a single mixing chamber. The mixing chamber has only one port for pressurized gas delivery and only one discharge port for gas-particulate mixture release.

The invention disclosed herein solves the following multiple significant shortcomings with devices that have no flow-control mechanisms and are solely dependent on flow-control mechanisms upstream of the mixing chamber:

1. When the external flow-control valve is initially activated, pressure waves propagate through the device as the mixing chamber builds up pressure. The largest pressure wave is caused at the instant the upstream flow is initiated. This is when the pressure gradient between the mixing chamber pressure and the pressurized-gas source is the greatest. This initial pressure wave causes a large amount of particulate matter to be agitated at once, thus causing an initial burst of abrasive to be released in a dense clump. This abrasive clump release causes an initial puff of abrasive that is inconsistent with the normal pace of particulate delivery during the device operation. This initial blast of abrasive may cause significant damage to the target surface by over etching.

2. Every time the external flow-control valve is activated, there is a delay in operational response as the gas-delivery tubing and mixing chamber pressures increase to the up-stream pressure. During this period of pressurization, the mixing action starts and the gas-particulate mixture progressively begins to flow out of the device. As the device reaches operational pressure level, steady gas-particulate mixture flow is established. This response delay in reaching steady flow at start up leads to discharge of abrasive material that does not possess the necessary particle velocity to perform useful etching. This loss of material leads to extra patient discomfort and more rapid depletion of the abrasive material.

3. Every time the upstream flow is terminated, the device continues to operate as the gas-delivery tubing and mixing chamber pressure is depleted. The period of depressurization is significant to the operation of the device since it reduces the responsiveness of the device to the user. This delay may damage the target surface by over etching as the device continues to dispense abrasive material after the user has turned off the pressurized-gas source controls. In operatory conditions, particulate matter may still be dispensed out of the devices as the dentist pulls the device out of the patient's mouth. This may expose the patient's eyes to the abrasive.

In fact, the Schur et al patent utilizes a check-valve for preventing gas flow in direction of the pressurized-gas source; hence forcing the device to continue operation as the mixing chamber pressure is reduced to ambient pressure.

In addition, since the operational control of these existing devices is dependent on external flow control mechanisms, performance levels of these devices vary between pressurized-gas sources. For these devices, the aggressiveness and precision of the etching is thus dependent on the external flow-control mechanism, and its abilities to regulate the upstream pressure and flow-rate. The device and method described herein eliminate the performance variation due to external flow-control mechanisms.

BRIEF SUMMARY OF THE INVENTION

Accordingly, several objects and advantages of the present invention are:

(a) to provide a device with means for precise single-hand regulation of the gas-abrasive flow independent of the external flow-control mechanism.

(b) to provide a device with instantaneous flow start-up response via an integral flow-control means that facilitate the continuous pressurization of the mixing chamber.

(c) to provide a device with instantaneous flow shut-off response via integral flow-control means that instantly terminates the flow out of the device without requiring the depressurization of the mixing chamber.

(d) to provide a device with better operational performance by eliminating puffs of abrasive during flow start-up.

(e) to provide a device with means for precisely regulating the gas-abrasive flow so a single device is able to operate in a wide range of applications, from light etching to drilling and cutting.

BRIEF DESCRIPTION OF THE SEVERAL VIEWS OF THE DRAWING

Various other objects, advantages, and features of the invention will become apparent to those skilled in the art from the following discussion taken in conjunction with the following drawings, where closely related figures have the same number but different alphabetic suffixes:

FIGS. 1, 2, and 3 are cross-sectional side views of the micro abrasive blasting device with integral flow-control means via displacement of the discharge conduit The pressurized-gas source is omitted.

FIGS. 4 and 5 are cross-sectional side views of the micro abrasive blasting device with integral flow-control means via displacement of the discharge conduit while the discharge conduit outlet remains stationary. The pressurized-gas source is omitted.

FIG. 6 a cross-sectional side view of the micro abrasive blasting device with integral flow-control means via deformation of the discharge conduit while the discharge conduit outlet remains stationary. The pressurized-gas source is omitted.

FIGS. 7, 8, and 9 are cross-sectional side views of the micro abrasive blasting device with integral flow-control means where deflection of the discharge conduit provides actuation restoring force while the discharge conduit outlet remains stationary. The pressurized-gas source is omitted.

FIG. 10 is a cross-sectional side view of the preferred embodiment where deflection of the discharge conduit provides actuation restoring force while the discharge conduit outlet remains stationary. The pressurized-gas source is omitted.

FIGS. 12 is cross-sectional side views of the preferred embodiment where an abrasive capturing filter is provided to prevent abrasive release during removal of the pressurized-gas source connector.

REFERENCE NUMERALS IN DRAWINGS

Figure 3A:
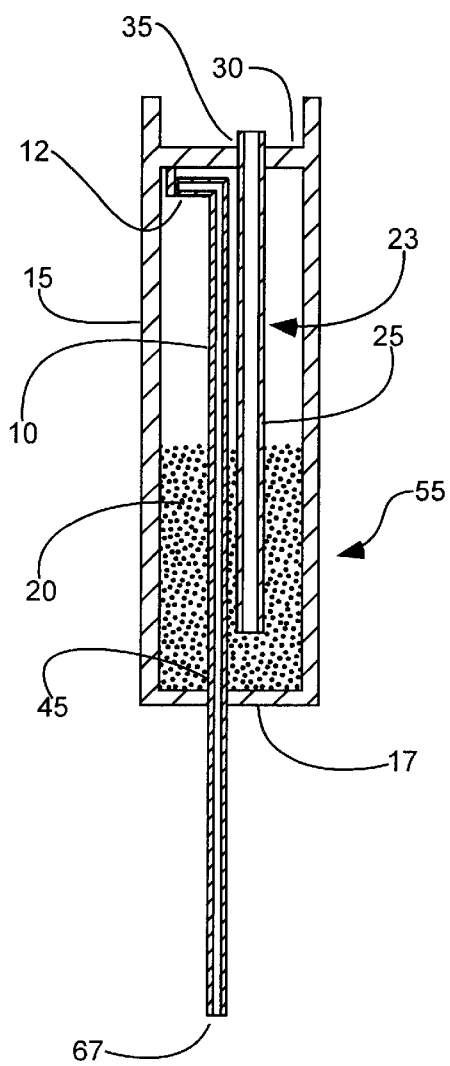

10 discharge conduit
11 discharge conduit mobile segment
12 discharge conduit inlet
15 mixing chamber side wall
17 mixing chamber first end wall
20 particulate matter
23 mixing chamber
25 gas-delivery conduit
30 mixing chamber second end wall
35 gas-receiving port
40 target material
45 discharge port
50 spring mechanism
55 micro abrasive blasting device
60 actuator mechanism
67 discharge conduit outlet
73 flexible tube
74 discharge conduit flexible segment
75 discharge nozzle
76 discharge conduit nozzle segment
80 travel-limiting stop 85 abrasive capturing filter
90 pressurized-gas source connector
95 flow rate sensitivity feature

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

Referring to FIG. 1A, a micro abrasive blasting device 55 is disclosed. The micro abrasive blasting device 55 includes a mixing chamber 23 having a mixing chamber side wall 15, a first end wall 17, and a second end wall 30. A particulate matter 20 is disposed in mixing chamber 23.

A gas-receiving port 35 is disposed in mixing chamber second end wall 30. A gas-delivery conduit 25 is in fluid communications with gas-receiving port 35, and extends through gas-receiving port 35 into mixing chamber 23.

A discharge port 45 is disposed in mixing chamber first end wall 17. A discharge conduit 10, elongated from discharge conduit inlet 12 to discharge conduit outlet 67, extends from mixing chamber second end wall 30 through discharge port 45 external to mixing chamber 23. Means are provided for the relative motion between discharge conduit 10 and discharge port 45, while maintaining discharge conduit 10 and discharge port 45 in fluid communications.

A spring mechanism 50 is attached to micro abrasive blasting device 55 externally to mixing chamber 23. Spring mechanism 50 applies a force onto discharge conduit 10 so discharge conduit inlet 12 abuts mixing chamber second end wall 30. As discharge conduit inlet 12 abuts mixing chamber second end wall 30, particulate matter 20 is prevented from entering discharge conduit 10.

The amount of sealing force S applied by spring mechanism 50 onto discharge conduit 10 is sufficient to maintain a seal between discharge conduit inlet 12 and mixing chamber second end wall 30 when mixing chamber 23 is pressurized. An actuator mechanism 60 is attached to micro abrasive blasting device 55 externally to mixing chamber 23 at one end, and to discharge conduit 10 at the other end. Actuator mechanism 60 provides means for counteracting the sealing force S applied on discharge conduit 10 by spring mechanism 50.

As pressurized-gas is supplied to micro abrasive blasting device 55 through gas-receiving port 35, mixing chamber 23 is pressurized. However, since discharge conduit inlet 12 abuts mixing chamber second end wall 30, pressurized-gas is not able to flow out of the device. Since no gas flow exists, no abrasive-gas mixing occurs in mixing chamber 23.

Referring to FIG. 1B, as force F is applied to actuator mechanism 60, actuator mechanism 60 counteracts sealing force S applied by spring mechanism 50. As force F generated by actuator mechanism 60 surmounts the sealing force S generated by spring mechanism 50, discharge conduit 10 is displaced. As discharge conduit 10 is displaced, discharge conduit inlet 12 moves away from mixing chamber second end wall 30, thus no longer abutting mixing chamber second wall 30. The opening of discharge conduit inlet 12 permits pressurized-gas inside mixing chamber 23 to instantly flow through discharge conduit 10. As flow is initiated, particulate matter 20 instantaneously mixes with the flowing gas and is dispensed through discharge conduit 10 to strike target material 40.

The position of discharge conduit 10 determines the distance between discharge conduit inlet 12 and mixing chamber second end wall 30. The gap between discharge conduit inlet 12 and mixing chamber second end wall 30 determines the gas-abrasive mixing and flow rate. Adjusting the gap between discharge conduit inlet 12 and mixing chamber second end wall 30, via discharge conduit 10 positioning, regulates these gas-abrasive flow characteristics.

As force F applied on actuator mechanism 60 is reduced, restoring force R applied by spring mechanism 50 on discharge conduit 10 displaces discharge conduit inlet 12 towards mixing chamber second end wall 30. When discharge conduit inlet 12 abuts mixing chamber second end wall 30 flow instantly terminates.

Figure 3B:
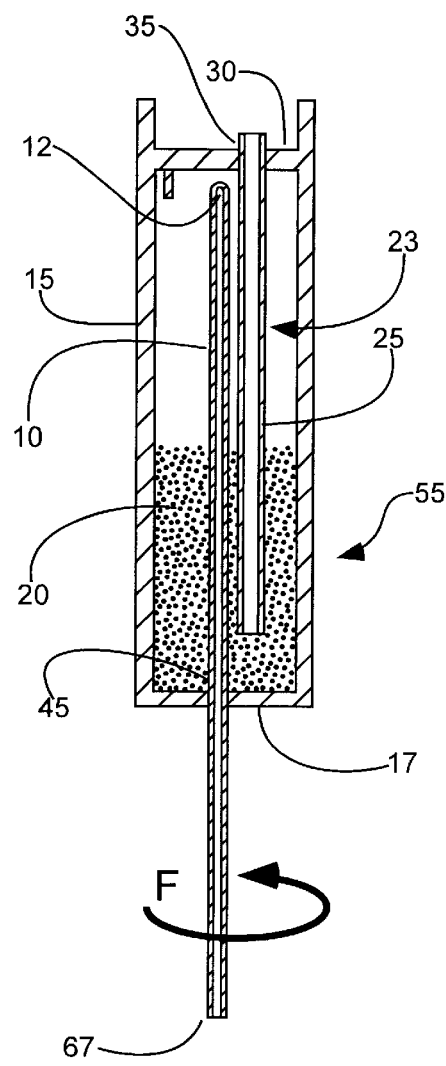

Although in the embodiment of FIG. 1 spring mechanism 50 provides means for abutting discharge conduit inlet 12 to mixing chamber second wall 30, many other types of known actuator mechanisms and force applicators can be utilized as well. In addition, as shown in FIG. 2, the displacement of discharge conduit inlet 12 away from mixing chamber second end wall 30 can also be attained by pivoting discharge conduit 10 about discharge port 45. As shown in FIG. 3, rotational displacement applied to discharge conduit 10 can also provide the necessary displacement to conduit inlet 12 to seal and unseal discharge conduit 10. Features for providing sealing surfaces could easily be attached to mixing chamber second end wall 30. Chamber side wall 15 could also be easily utilized as sealing surfaces. Although not shown, the embodiments in FIGS. 2 and 3 also require force applicator mechanisms for abutting discharge conduit inlet 12 to mixing chamber second end wall 30, and controlling the displacement of discharge conduit 10.

The embodiments shown in FIGS. 1, 2, and 3 achieve the desired goal of providing an integral flow-control mechanism down-stream of the mixing chamber that is controllable during device operation with a single-hand. However, these embodiments have the undesirable affect that the distance between the discharge conduit outlet 67 and target material 40 varies with position of the discharge conduit 10. In other words, the distance of discharge conduit outlet 67 to target material 40 varies as the user adjusts the flow-control. These embodiments also require force applicator mechanisms to abut discharge conduit inlet 12 to mixing chamber second end wall 30. The following disclosed embodiments provide improvements that address these shortcomings.

Referring to FIG. 4A, a discharge nozzle 75 is mounted onto micro abrasive blasting device 55 external to mixing chamber 23. Discharge nozzle 75 extends in fluid communication through discharge conduit outlet 67 into discharge conduit 10. Referring to FIG. 4B, as force F is applied to actuator mechanism 60, discharge conduit 10 is displaced sliding over discharge nozzle 75. As discharge conduit inlet 12 opens via displacement of discharge conduit 10, discharge nozzle 75 remains stationary with respect to target material 40. The gas-particulate mixture flows through discharge conduit 10 and discharge nozzle 75 to strike target material 40. Of course as a design choice, it is possible to have discharge conduit 10 extend into discharge nozzle 75.

Figure 5A:
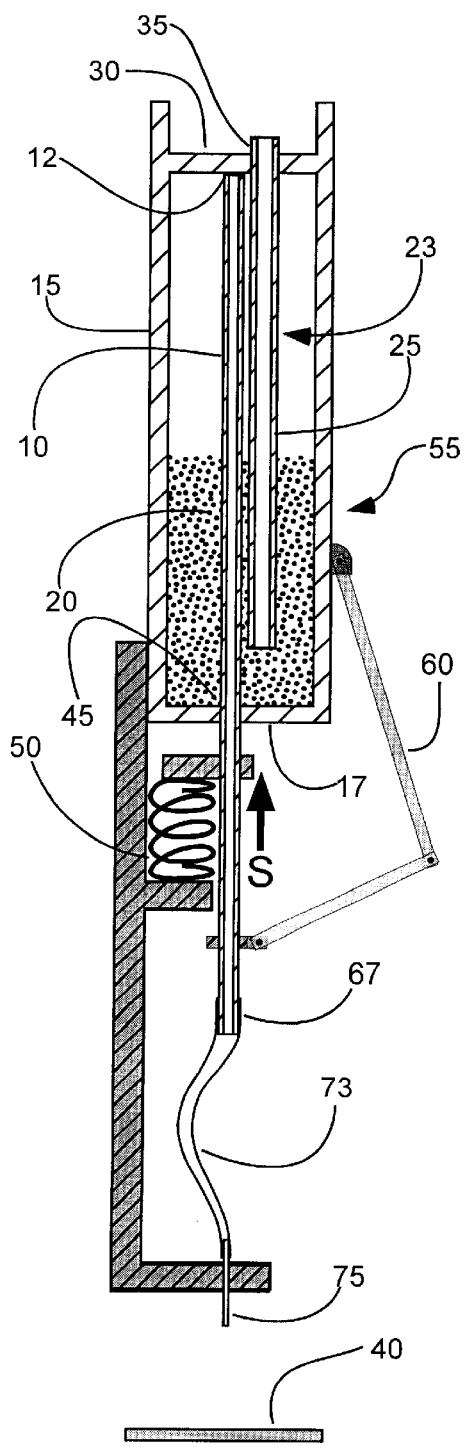
Figure 5B:
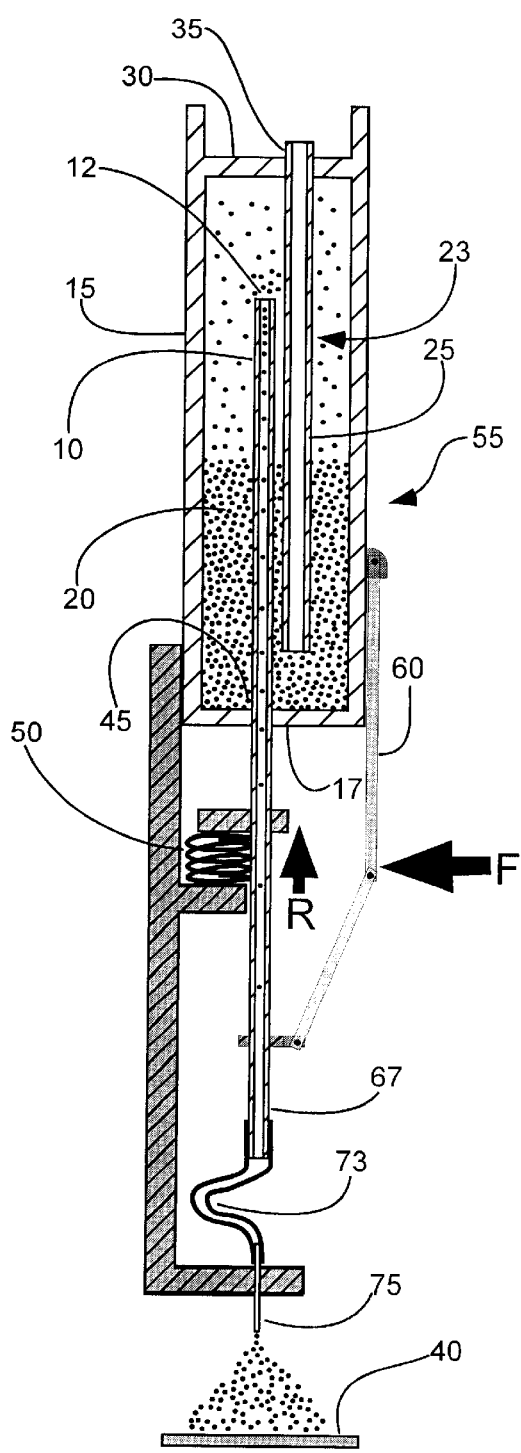

Referring to FIG. 5A, a discharge nozzle 75 is mounted onto micro abrasive blasting device 55 external to mixing chamber 23. A flexible tube 73 connects to discharge conduit outlet 67 at one end and to discharge nozzle 75 at the other end. Referring to FIG. 5B, as force F is applied to actuator mechanism 60, discharge conduit 10 is displaced. As discharge conduit 10 is displaced, flexible tube 73 is flexed as it travels with discharge conduit outlet 67. The gas-particulate mixture flows through discharge conduit 10, flexible tube 73, and discharge nozzle 75 to strike target material 40. As discharge conduit inlet 12 opens via displacement of discharge conduit 10, discharge nozzle 75 remains stationary with respect to target material 40.

Referring to FIG. 6A, actuator mechanism 60 is utilized to pinch flexible tube 73 to create a flow regulator thus eliminating the need for the displacement of discharge conduit 10. Spring mechanism 50 applies a sealing force S on actuator mechanism 60 that causes flexible tube 73 to collapse shut thus facilitating the continuous pressurization of mixing chamber 23. Referring to FIG. 6B, as force F is applied to actuator mechanism 60, actuator mechanism 60 counteracts sealing force S applied by spring mechanism 50. As the force F generated by actuator mechanism 60 surmounts the sealing force S generated by spring mechanism 50, flexible tube 73 opens to permit flow. The position of actuator mechanism 60 determines the size of the flexible tube 73 opening and thus gas-abrasive mixing and flow rate.

Referring to FIG. 7, the resistance of discharge conduit 10 to deflection is utilized to replace spring mechanism 50. The resistance of discharge conduit 10 to deflection applies sealing force S on actuator mechanism 60 that causes flexible tube 73 to collapse shut. As force F is applied to actuator mechanism 60, actuator mechanism 60 counteracts sealing force S applied by the deflection of discharge conduit 10. As force F generated by actuator mechanism 60 surmounts sealing force S generated by the deflection of discharge conduit 10, flexible tube 73 opens to permit flow. As force F is removed from actuator mechanism 60, the deflection of discharge conduit 10 provides restoring force R on actuator mechanism 60 to collapse shut and reseal flexible tube 73.

Of course as a design choice discharge conduit 10, flexible tube 73, and discharge nozzle 75 could be integrated into a single contiguous conduit. In such a case, the deformation of discharge conduit 10 regulates the gas-abrasive flow characteristics while the deflection properties of discharge conduit 10 provides a both sealing and restoring force.

In the embodiments of FIGS. 6 and 7 having the flow regulation downstream of the discharge conduit inlet 12 is a disadvantage. It is a disadvantage since abrasive material 20 is able to get into discharge conduit 10 without mixing with the pressurized-gas. Abrasive material can propagate into discharge conduit 10 prior to use or during use. Additionally, when flow is terminated, the quantity of particulate matter 20 already mixed with the pressurized-gas and located in discharge conduit 10 portion upstream of the regulator settles. This trapped material is released when pressurized-gas is applied to the device. Since the abrasive particles trapped in discharge conduit 10 do not go through the mixing chamber, the initial pressurized-gas application causes the trapped abrasive to be released in a dense clump. This abrasive clump release causes an initial puff of abrasive that is inconsistent with the normal pace of particulate delivery during the device operation. This initial blast of abrasive may also damage the target surface by over etching.

FIGS. 8 and 9 present innovative embodiments where actuator mechanism 60 protrudes into mixing chamber 23 to deflect discharge conduit 10. The deflection of discharge conduit 10 provides means for both regulating the gas-abrasive flow via displacement of discharge conduit inlet 12 and applying restoring force R to actuator mechanism 60 while maintaining discharge conduit outlet 67 stationary. These embodiments have the added benefit that no relative motion between discharge conduit 10 and discharge port 45 is required.

Referring to FIG. 9, the regulation of the gas-abrasive flow via displacement of discharge conduit inlet 12 is accomplished by varying the gap between discharge conduit inlet 12 and the chamber side wall 15.

Referring to the preferred embodiment of FIG. 10A, a contiguous discharge conduit 10 eliminates spring mechanism 50 while providing an integrated flow-control mechanism, via displacement of discharge conduit inlet 12; and while providing a stationary discharge conduit outlet independent of discharge conduit inlet 12 position. In this preferred embodiment, discharge conduit 10 consists of discharge conduit mobile segment 11, discharge conduit flexible segment 74, and discharge conduit nozzle segment 76. Discharge conduit mobile segment 11 extends from mixing chamber second end wall 30 through discharge port 45 external to mixing chamber 23. Means are provided for the relative motion between discharge conduit mobile segment 11 and discharge port 45, while maintaining discharge conduit mobile segment 11 and discharge port 45 in fluid communications.

Discharge conduit nozzle segment 76 of discharge conduit 10 is mounted onto micro abrasive blasting device 55 external to mixing chamber 23. Discharge conduit flexible segment 74 extends from the termination of discharge conduit mobile segment 11 to discharge conduit nozzle segment 76. Discharge conduit flexible segment 74 is preferably shaped as a coil compression spring. The deflection of the coiled discharge conduit flexible segment 74 generates a compression force that resists deflection. Discharge conduit flexible segment 74 preferably applies sealing force S onto discharge conduit mobile segment 11 so discharge conduit inlet 12 abuts mixing chamber second end wall 30. The amount of sealing force S applied by the coiled section is sufficient to maintain a seal between discharge conduit inlet 12 and mixing chamber second end wall 30 when mixing chamber 23 is pressurized.

An actuator mechanism 60 is attached to micro abrasive blasting device 55 externally to mixing chamber 23 at one end, and preferably attached to discharge conduit mobile segment 11 at the other end. Actuator mechanism 60 provides means for counteracting the compression force applied on discharge conduit mobile segment 11 by discharge conduit flexible segment 74. Referring to FIG. 10B, as force F is applied to actuator mechanism 60, discharge conduit mobile segment 11 is displaced. As the discharge conduit mobile segment 11 is displaced, discharge conduit flexible segment 74 is flexed as it travels at one end with discharge conduit mobile segment 11 and held stationary by discharge conduit nozzle segment 76 at the other end. As discharge conduit mobile segment 11 is displaced, discharge conduit inlet 12 moves away from mixing chamber second end wall 30, thus no longer abutting mixing chamber second wall 30.

The opening of discharge conduit inlet 12 permits pressurized-gas inside mixing chamber 23 to instantly flow into discharge conduit 10. As flow is initiated, particulate matter 20 instantaneously mixes with the flowing gas and is dispensed through discharge conduit mobile segment 11, discharge conduit flexible segment 74, discharge conduit nozzle segment 76, and out of discharge conduit outlet 67 to strike target material 40.

Referring to FIG. 10C, the position of discharge conduit mobile segment 11 determines the distance between discharge conduit inlet 12 and mixing chamber second end wall 30. The gap between discharge conduit inlet 12 and mixing chamber second end wall 30 determines the gas-abrasive mixing and flow rate. Adjusting the gap between discharge conduit inlet 12 and mixing chamber second end wall 30, via discharge conduit mobile segment 11 positioning, regulates these gas-abrasive flow characteristics.

As the force F applied to actuator mechanism 60 is reduced, restoring force R applied by the deflection of discharge conduit flexible segment 74 displaces discharge conduit mobile segment 11 towards mixing chamber second wall 30. When discharge conduit inlet 12 abuts mixing chamber second end wall 30 flow instantly terminates.

Although discharge conduit flexible segment 74 is presented in the shape of a coil compression spring, discharge conduit flexible segment 74 can have many combinations of geometric shapes and materials that provide the necessary flexibility. This flexibility provides deflection properties that generate the required sealing force S—so discharge conduit inlet 12 abuts mixing chamber second end wall 30, and an actuator restoring force R—to resist the force F applied by actuator mechanism 60.

Figure 11A:
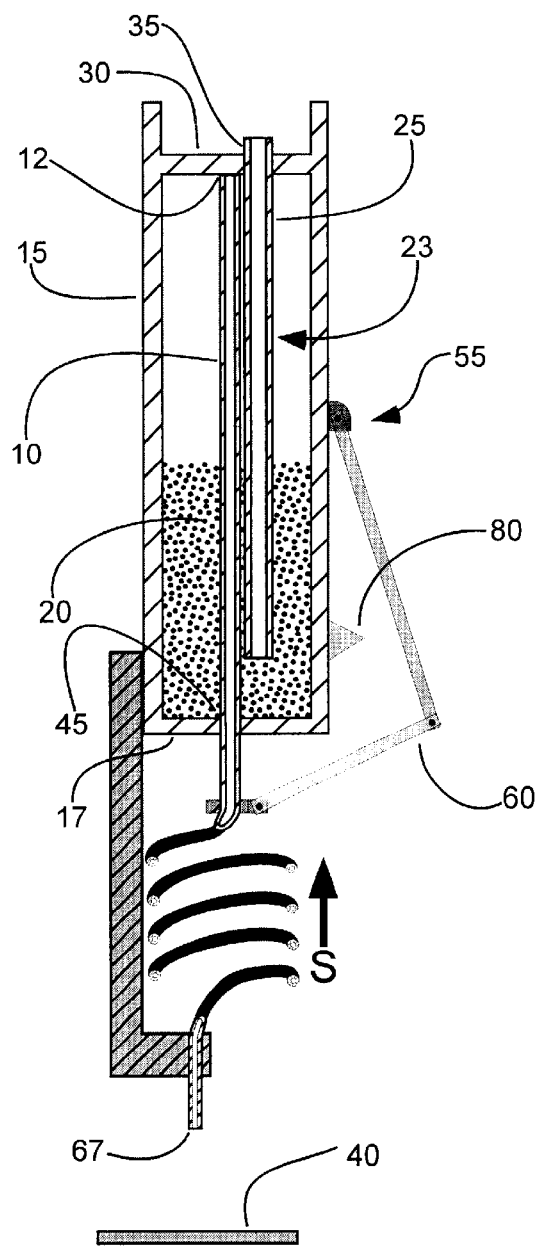
FIGS. 11 is a cross-sectional side view of the preferred embodiment where the travel of the flow-control lever is limited. The pressurized-gas source is omitted.
Figure 11B:
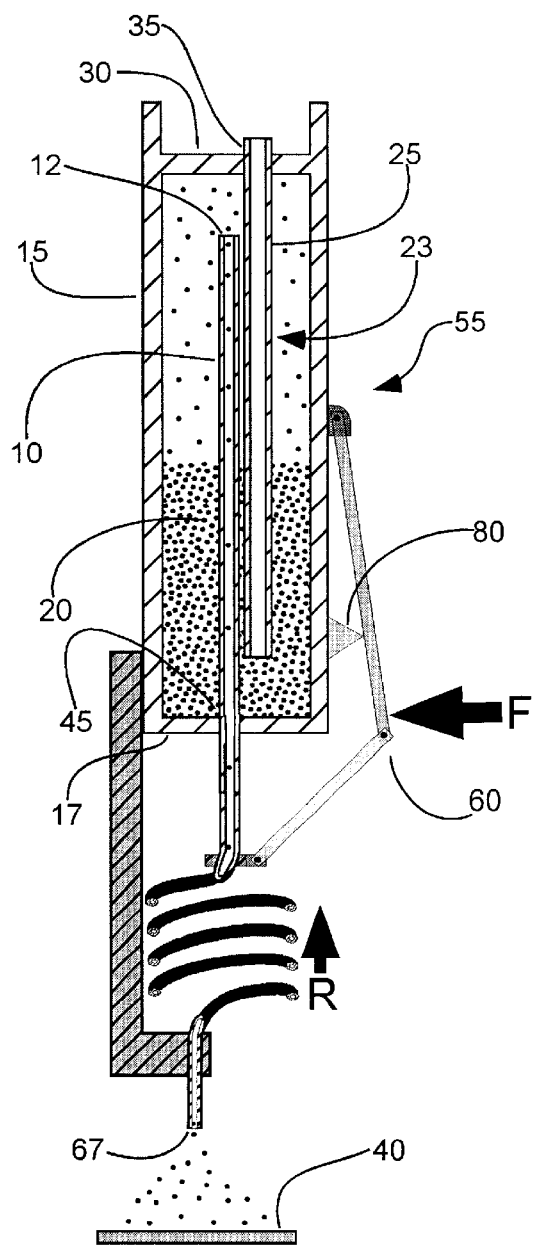
Figure 13A:
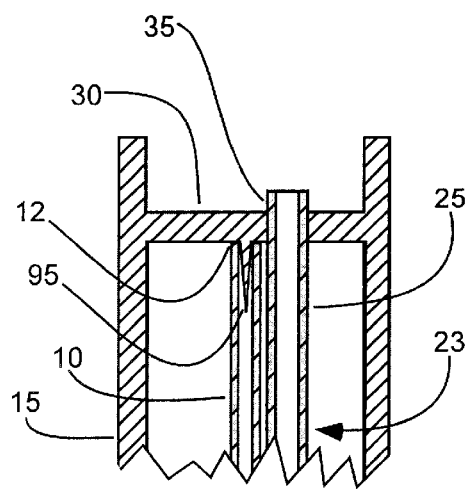
FIGS. 13 cross-sectional side views of the preferred embodiment where a feature is provided on mixing chamber wall to increase the sensitivity of flow rate regulation. The particulate matter is omitted.
Figure 13B:
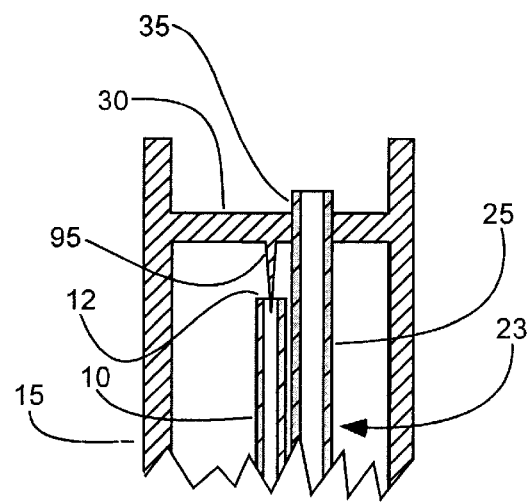

FIGS. 11, 12, and 13 present three additional enhancements to the preferred embodiment of FIG. 10. Referring to FIG. 11, the first enhancement is a travel-limiting stop 80 mounted externally to mixing chamber 23 that restricts the movement of actuator mechanism 60. Restricting the movement of actuator mechanism 60 limits the gap opening between discharge conduit inlet 12 and mixing chamber second end wall 30, thus restricting the etching rate of the device. Travel-limiting stop 80 is most useful for delicate operations where over etching could cause damage to target material 40. It is preferable that travel-limiting stop 80 is made to be adjustable by the user, so a single device is able to perform in the entire range of etching rates.

FIG. 12 discloses a second enhancement, the use of an abrasive capturing filter 85 located upstream of mixing chamber 23. Abrasive capturing filter 85 is utilized to stop particulate matter 20 from exiting micro abrasive blasting device 55 during the removal of pressurized-gas source connector 90 from the micro abrasive blasting device 55. Since discharge conduit inlet 12 abuts mixing chamber second end wall 30, mixing chamber 23 remains pressurized once pressurized-gas is delivered via pressurized-gas source connector 90. As pressurized-gas source connector 90 is removed from micro abrasive blasting device 55, mixing chamber 23 depressurizes via gas-delivery conduit 25. The depressurization via gas-delivery conduit 25 drives particulate matter 20 out of mixing chamber 23 through gas-delivery conduit 25. Abrasive capturing filter 85 is utilized to stop particulate matter 20 from exiting micro abrasive blasting device 55. The type and location of the abrasive capturing filter is a design choice. Various types and shapes of filters could be utilized to integrate abrasive capturing filter 85 into gas-delivery conduit 25 or mixing chamber 23.

FIG. 13 discloses a third enhancement to the preferred embodiment for improving the flow rate regulation sensitivity of micro abrasive blasting device 55. A flow rate sensitivity feature 95 is provided on mixing chamber second end wall 30. Flow rate sensitivity feature 95 facilitates a slower gap opening between mixing chamber second end wall 30 and discharge conduit inlet 12. As discharge conduit 10 is displaced, a slower gap opening is achieved by controlling the exposed inlet area of discharge conduit inlet 12. The preferred shape of the flow rate sensitivity feature 95 provides a linear relationship between the displacement of discharge conduit 10 and the exposed inlet area of discharge conduit inlet 12.

From the description above, the following advantages of the present invention become evident:
(a) Providing flow regulation downstream of the mixing chamber
  (I) facilitates the continuous pressurization of the mixing chamber and therefore provides instantaneous operation start-up response.
  (II) terminates the flow out of the device instantly without requiring the depressurization of the mixing chamber.
  (III) facilitates the regulation the gas-abrasive flow independently of the external flow-control mechanism.
(b) Providing a discharge conduit with a displaceable inlet
  (I) eliminates puffs of abrasive during operation start-up thereby providing a device with better operational performance.
  (II) provides for precise flow control so a single device is able to operate in a wide range of applications, from light etching to drilling and cutting.
(c) Providing a discharge conduit with a flexible segment
  (I) provides means for a stationary discharge conduit outlet with respect to the target material that is independent of discharge conduit displacement.
  (II) provides means for flow control downstream of the mixing chamber via deformation of the discharge conduit.
(d) Providing a discharge conduit with a flexible segment that resist deformation
  (I) provides means for generating a sealing force that abuts the discharge conduit inlet to mixing chamber wall.
  (II) provides means for generating an actuator restoring force that counteracts the displacement force applied on the discharge conduit.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

SUMMARY, RAMIFICATION, AND SCOPE

The present invention accomplishes the above-stated objectives, as well as others, as may be determined by a fair reading and interpretation of the entire specification.

Accordingly, the reader will see that the present invention is a superior micro abrasive blasting device with integral flow control. The disclosed device provides means for precise single-hand regulation of the gas-abrasive flow, independently of external pressurized-gas source controls. The flow-control method provides for the continuous pressurization of the mixing chamber that yields instantaneous flow start-up response and instantaneous flow shut-off response. The preferred device offers superior operational performance by eliminating puffs of abrasive during operation start-up, while providing precise gas-abrasive flow regulation so a single device is able to operate in a wide range of applications, from light etching to drilling and cutting.

Furthermore, the present invention has the additional advantages in that
- it provides a simple device where the discharge conduit deflects to provide a stationary discharge conduit outlet.
- it provides a simple device where the discharge conduit deflection is utilized to generate a sealing force and a restoring force.

Thus the scope of the invention should be determined by the appended claims and their legal equivalents, rather than by the examples given.

What I claim as my invention is:

1. A micro abrasive blasting device, comprising:
   a chamber having a side wall, a first end wall at one end of the chamber and a second end wall at an opposite end of the chamber;
   a gas-receiving port in said second end wall;
   a gas-delivery conduit disposed within said chamber and extending in fluid communications from said gas-receiving port towards said first end wall;
   a discharge port in the first end wall;
   a discharge conduit disposed within the chamber and extending in fluid communications through said discharge port external to the chamber;
   wherein means for flow control is located on said discharge conduit.

2. The apparatus, according to claim 1, wherein:
   the chamber second end wall is a removable cap.

3. The apparatus, according to claim 1, wherein:
   said flow control means prevents depressurization of the chamber.

4. The apparatus, according to claim 1, wherein:
   deformation of the discharge conduit provides means for flow control.

5. The apparatus, according to claim 1, wherein:
   deflection of the discharge conduit provides means for controlling the opening to the discharge conduit inlet.

6. The apparatus, according to claim 1, wherein:
   deflection of the discharge conduit provides actuation force means for flow control.

7. The apparatus, according to claim 1, wherein:
   deflection of the discharge conduit provides means for maintaining the discharge conduit outlet stationary.

8. A micro abrasive blasting device, comprising:
   a chamber having a side wall, a first end wall at one end of the chamber and a second end wall at an opposite end of the chamber;
   a gas-receiving port in said second end wall;
   a gas-delivery conduit disposed within said chamber and extending in fluid communications from said gas-receiving port towards said first end wall;
   a discharge port in the first end wall;
   a discharge conduit in fluid communications with said discharge port, extending from the second end wall and/or said side wall through the discharge port external to the chamber;
   means for displacing and/or rotating said discharge conduit inlet;
   wherein displacement and/or rotation of the discharge conduit provides means for controlling the opening to the discharge conduit inlet.

9. The apparatus, according to claim 8, wherein:
   the chamber second end wall is a removable cap.

10. The apparatus, according to claim 8, wherein:
    the distance between discharge conduit inlet and second end wall and/or side wall provides means for flow control.

11. The apparatus, according to claim 8, wherein:
    deflection of the discharge conduit provides a sealing force between discharge conduit inlet and second end wall and/or side wall.

12. The apparatus, according to claim 8, wherein:
    deflection of the discharge conduit provides a displacement restoring force on the discharge conduit.

13. The apparatus, according to claim 8, wherein:
    deflection of the discharge conduit provides means for maintaining the discharge conduit outlet stationary.

14. The apparatus, according to claim 8, wherein:
    a travel-limiting stop restricts the opening to the discharge conduit inlet.

15. The apparatus, according to claim 8, wherein:
    a flow rate sensitivity enhancing feature on second end wall and/or side wall protrudes into discharge conduit inlet.

16. The apparatus, according to claim 8, wherein:
    an abrasive capturing filter is located upstream of the chamber.

17. A method for flow control of a micro abrasive blasting device, comprising:
    a chamber having a side wall, a first end wall at one end of the chamber and a second end wall at an opposite end of the chamber;
    a gas-receiving port in the second end wall;
    a gas-delivery conduit disposed within the chamber and extending in fluid communications from said gas-receiving port towards the first end wall;
    a discharge port in the first end wall;
    a discharge conduit in fluid communications with said discharge port, extending from said second end wall and/or said side wall through the discharge port external to the chamber;
    means for deflecting said discharge conduit;
    wherein deflection of the discharge conduit provides means for controlling the opening to the discharge conduit inlet while maintaining discharge conduit outlet stationary.

18. The method, according to claim 17, wherein:
    the chamber second end wall is a removable cap.

19. The method, according to claim 17, wherein:
    deflection of the discharge conduit provides a sealing force between discharge conduit inlet and second end wall and/or the side wall.

20. The method, according to claim 17, wherein:
    deflection of the discharge conduit provides a displacement restoring force on the discharge conduit.

21. The method, according to claim 17, wherein:
    a travel-limiting stop restricts the opening to the discharge conduit inlet.

* * * * *